United States Patent
Schmidt et al.

[19]

[11] Patent Number: 6,030,351
[45] Date of Patent: Feb. 29, 2000

[54] PRESSURE RELIEF REMINDER AND COMPLIANCE SYSTEM

[75] Inventors: Robert N. Schmidt; Jamison J. Float, both of Cleveland; Steven P. Hendrix, Sagamore Hills, all of Ohio

[73] Assignee: Cleveland Medical Devices Inc., Cleveland, Ohio

[21] Appl. No.: 09/105,807

[22] Filed: Jun. 26, 1998

[51] Int. Cl.$^7$ .................................................. A61B 5/00
[52] U.S. Cl. ........................................ 600/592; 600/595
[58] Field of Search ................................. 600/587, 592, 600/595; 73/862.625

[56] References Cited

U.S. PATENT DOCUMENTS

| | | | |
|---|---|---|---|
| 4,554,930 | 11/1985 | Kress | 128/774 |
| 4,869,265 | 9/1989 | McEwen | 128/774 |
| 5,042,504 | 8/1991 | Huberti | 128/779 |
| 5,253,656 | 10/1993 | Rincoe et al. | 128/782 |
| 5,408,873 | 4/1995 | Schmidt et al. | 600/592 |
| 5,619,186 | 4/1997 | Schmidt et al. | 340/573 |

OTHER PUBLICATIONS

Klein, et al., "Pressure Relief Training Device: The Microcalculator", Arch Phys Med Rehabil, vol. 62, Oct. 1981, pp. 500, 501.

Merbitz, et al. "Wheelchair Push–ups: Measuring Pressure Relief Frequency", Arch Phys Med Rehabil, vol. 66, Jul. 1985, pp. 433–438.

*Primary Examiner*—Max Hindenburg
*Attorney, Agent, or Firm*—John H. Vynalek

[57] ABSTRACT

A pressure relief reminder and compliance system and method to prevent the formation of pressure sores on a person's skin is disclosed. The system comprises sensor which responds according to pressure exerted on the skin; a programmable microcontroller connected to the sensor; means for programming the microcontroller; and indicating means. A programming device operates software to changeably program the microcontroller with certain values of pressure and time, such that the level and duration of pressure on the skin and the duration of the absence of pressure thereon, are compared to the programmed values, is given to the wheelchair user, and the levels and duration of pressure are stored in memory. The programming device also can download from the memory the recorded values for review and analysis by a physician, clinician, therapist or other health professional. The indicators can be an audible alarm, like a beeper or buzzer, or a vibrator.

A method for training a person to reduce the incidence of pressure sores occurring due to pressure exerted on the skin for a certain duration is also disclosed. The method comprises the steps of determining a specific maximum pressure position duration and a minimum pressure relief position duration for that person; measuring the duration of the person in a pressure position; alerting the person when the duration of the pressure position equals the maximum pressure position duration; alarming the person when the duration of the pressure position exceeds the maximum pressure position duration; continuing the alarming until the person is in a pressure relief position; measuring the duration of the pressure position; and prompting the person to continue the pressure relief position until the duration thereof equals the minimum pressure relief duration.

16 Claims, 4 Drawing Sheets

PRESSURE RELIEF REMINDER AND COMPLIANCE SYSTEM

STATEMENT REGARDING FEDERALLY SPONSORED RESEARCH OR DEVELOPMENT

This invention was made with Government support under Grant No. 1 R43 HD35023-01 awarded by the National Institute of Child Health and Human Development. The Government has certain rights in the invention.

BACKGROUND OF THE INVENTION

1. Field of the Invention

The present invention relates, generally, to instruments for measuring and monitoring the pressure exerted on a person's skin, and, more particularly, to pressure measuring and monitoring instruments which are programmable and provide indication when the level and duration of pressure reach certain values.

2. Description of Related Art

The skin of people confined to a bed or wheelchair is susceptible to decubitus ulcers, commonly referred to as pressure sores or bed sores. This susceptibility is generally due to a level of pressure being exerted on an area, particularly a bony prominence, for an excessive duration of time. The pressure occludes the capillaries, cutting off the blood supply, causing necrosis of the tissue. Ordinarily, people with normal range of movement and sensation adjust or shift their weight to relieve such pressure prior to the formation of such sores. People who are bedridden, though, although they may have sensation, may not have an adequate range of movement and, therefore, cannot as easily adjust or shift their weight. People confined to a wheelchair, paraplegics for example, may be able to adjust or shift their weight but do not have sensation to indicate that it is time to do so. People with insensate feet, diabetics for instance, develop pressure sores which may ultimately result in amputation. Additionally, a person's susceptibility to the formation of such sores is dependent, to a certain extent, on tissue condition.

The most effective way to ameliorate the impact of pressure or bed sores is to preclude their formation. For bedridden persons this requires another person, like a nurse or other care giver, to periodically move or shift the bedridden person at the first sign of discomfort. For paraplegics and diabetics, though, because of their insensate condition, there is no sign of discomfort. In addition, diabetics with insensate feet tend to develop calluses at the pressure points on their feet aggravating the condition. Therefore, some external indication must be communicated to the paraplegic and the diabetic that it is time to shift or move or get off their feet. For the paraplegic, simply periodically raising themselves slightly from the wheelchair seat by pushing themselves up using their arms on the wheel chair handles or wheels ("pressure-relief") can preclude the formation of pressure sores. For the diabetic, sitting or in some way removing the weight from the foot achieves the same result. Although pressure-relief is simple to perform and very successful in the prevention of pressure sores, to be effective, the practice must become a life-long habit. A significant number of paraplegics, though, abandon the practice after leaving a hospital. This is due, mainly, to their lack of discipline and the possible embarrassment that may be caused by traditional reminder devices. For diabetics, there exists no suitable device or system to remind of the need for a pressure relief.

It is necessary, therefore, not only to adequately train a person in a pressure-relief technique but also to provide the person with a device that continually reinforces such training to instill in the person a life-long behavioral pattern and one that operates in accordance with a person's specific physical characteristics and needs. Inherent in this is the interaction of a physician, clinician and/or therapist who can adjust the device according to the specific needs, train the person in the proper pressure-relief technique and review, monitor and analyze the progress the person is making in relieving the pressure. This requires not only a means for monitoring the level and duration of pressure and indicating when relief must be performed, but also a means for recording and logging the person's pressure-relief attempts and successes.

U.S. Pat. No. 4,554,930 to Kress (abandoned), teaches a pressure sensing device and method for preventing ulcer formation. The device and method in Kress, though, are based on a fixed, predetermined level of pressure and time which cannot be changed. In other words, it is a one-size-fits-all device. The device is not programmable nor does it record the person's attempts to relieve the pressure and the duration of such pressure or relief In addition, there is no ability for a physician, clinician or therapist to review or analyze the activity of the person. There is no way to feed back to the person or the physician information which discloses and details the efforts of the person in relieving the pressure.

The need to adjust or program a device or system to fit a patient's particular circumstances was fully explained by Charles T. Merbitz et al., *Wheelchair Push-ups: Measuring Pressure Relief Frequency*, Arch Physician Medical Rehabilitation Vol. 66, July 1985. On page 9, the authors discuss how their findings suggest the need for an "individual prescription of inter-lift-off intervals for a given patient". For their study the authors utilized a rudimentary device involving air bladders with a lever to indicate when a certain threshold was reached. The device was not programmable or adjustable for a particular patient, but adequately illustrated the need for same.

U.S. Pat. No. 5,253,656 to Rincoe et al., teaches an apparatus and method for monitoring pressure between the surface of a body part and a contact surface. The device in Rincoe et al. teaches the reading of a plurality of pressure sensors by a microcomputer, through interface circuitry, which then develops a force profile from the readings. The pressure sensors are arranged in a column and row array and are read through a multiplexing process utilizing unique addresses for each sensor. The microcomputer, a personal computer, controls the apparatus with instructions inputted through a keyboard with the force profile visually presented on the computer display. The apparatus, therefore, is designed such that the personal computer must be attached to the pressure sensors in order for it to operate. Accordingly, the subject, usually a patient, is continuously tethered to the computer eliminating any mobility and restricting the times in which the apparatus actually performs any monitoring.

U.S. Pat. No. 5,042,504 to Huberti teaches a device for monitoring loads exerted on parts of the body. The Huberti device requires that a load-related parameter be measured and raw data representing that parameter be generated. The raw data is the output from the sensor corresponding to the force measured thereby which is entered into memory and plotted over time. The raw data is compared to analysis data and reference data, also inputted into memory, to produce a visual representation comparing the raw data, analysis data and reference data. This type of complex data inputting and comparing is appropriate for applications involving dynamic loading of extremities during rehabilitation. In fact, Huberti is specifically drawn to foot weight sensing where load profiling is necessary in order to assure the optimal healing of injured legs or the proper placement and use of prosthetic devices. It does not provide the required utility for pressure or bed sore prevention.

U.S. Pat. No. 5,619,186 to Schmidt et al. describes a foot weight alarm device that senses the dynamic forces exerted on a foot, develops a digital value corresponding to such force and provides an alarm when the force exceeds a certain level or range. The device of this patent, though, does not take into account any duration of loading or non-loading and like the device in Huberti does not provide the appropriate utility for pressure sore prevention.

Accordingly, a need exists for a system and device which can be used by a physician, clinician and/or therapist to develop the appropriate pressure level and duration for a particular person and to train a person in the proper technique and timing of a pressure-relief, which provides to the person an indication of the need for a pressure-relief and does so in an unobtrusive and non-embarrassing manner; which provides a record or log of the person's pressure-relief attempts and successes so that the person's pressure relief activities can be reviewed and the training periodically reinforced; and is light weight, mobile and easy to use.

BRIEF SUMMARY OF THE INVENTION

The present invention provides a method and apparatus to satisfy the aforementioned need.

It is an object of the present invention to provide a system which can be used by a physician, clinician and/or therapist to develop the appropriate pressure level and duration for a particular patient.

Another object of the present invention to provide a system and method which can be used by a physician, clinician and/or therapist to train a patient in the proper technique and frequency of pressure-reliefs.

Still a further object of the present invention is to provide a system which provides to the user an indication of the need for a pressure-relief and does so in an unobtrusive and non-embarrassing manner.

Still a further object of the present invention is to provide a system which provides a record or log of the person's pressure-relief activities so that the person's activities can be reviewed and the training periodically reinforced.

Still a further object of the present invention is to provide a system which is light weight, mobile and easy to use.

Accordingly, the present invention relates to a pressure relief reminder and compliance system, comprising a sensor which responds according to pressure exerted on the skin; a programmable microcontroller connected to the sensor; means for programming the microcontroller; and indicating means. The means for programming operates software to changeably program the microcontroller with certain values of pressure and time, such that the level and duration of pressure on the skin and the duration of the absence of pressure thereon, are compared to the programmed values, appropriate indication is given to the wheelchair user, and the levels and durations of pressure are stored in memory. A personal computer can be used as the means for programming and also can download from the memory the recorded values for review and analysis by a physician, clinician, therapist or other health care professional. The indicating means can be an audible alarm, like a buzzer or a vibrator. A silencing push button is also included in the event the user intends to deactivate the audible alarm. Interfacing means are provided between the microcontroller and the means for programming.

In another aspect, the present invention relates to a method for training a person to reduce the incidence of pressure sores occurring due to pressure exerted on the skin for a certain duration, comprising the steps of determining a specific maximum pressure duration and a minimum pressure relief duration for that person; measuring the duration of the person while pressure is exerted to the skin; alerting the person when the duration of the pressure equals the maximum pressure duration; alarming the person when the duration of the pressure exceeds the maximum pressure duration; continuing the alarming until the person is in a pressure relief position; measuring the duration of the pressure relief, and prompting the person to continue the pressure relief position until the duration thereof equals the minimum pressure relief duration.

BRIEF DESCRIPTION OF THE SEVERAL VIEWS OF THE DRAWINGS

Further features of the present invention will become apparent to those skilled in the art to which the present invention relates from reading the following specification with reference to the accompanying drawings in which.

DETAILED DESCRIPTION OF THE INVENTION

Figure 1:
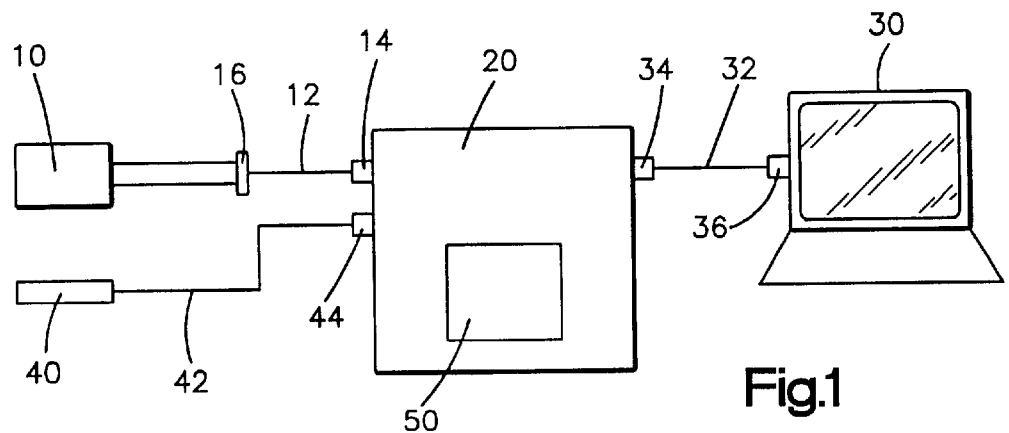
FIG. 1 is a view showing the schematic representation of the present invention and its interconnections

Referring now to FIG. 1 there is shown a schematic representation of the present invention. Sensor 10 responds according to pressure exerted on a person's skin. The sensor 10 is placed at a probable high pressure point, for instance, under the seat cushion on a wheelchair of a paraplegic at the points where the ischial tuberosity, coccyx and/or trochanter locate when a paraplegic is seated on the wheelchair. For a diabetic it can be located on the heal, hallux or metatarsal heads. Advantageously, multiple sensors 10 may be used. It is not necessary that the sensor 10 be in actual contact with the skin of the person in order for it to adequately respond to a pressure exerted on the skin. The sensor 10 can be placed on top of the seat cushion beneath the clothing of a person, under a seat cushion or the person's sock without affecting operation. This is accomplished by properly setting the pressure for the sensor allowing for the pressure distribution through the seat cushion or clothing. The sensor 10 sends a signal corresponding to the pressure exerted on the sensor 10 to a microcontroller 200 (not shown) by way of the sensor lead 12. The sensor lead 12 terminates at one end with sensor connector 14 for connection to the controller housing 20. The lead connector 16 can be optionally added to reduce the size of the sensor 10 thereby reducing the cost when the sensor 10 needs to be replaced. The sensor connector 14 can be a 2.5 mm sub-miniature mono phono plug. In a certain applications, two sensors 10 can be used in which case the sensor connector 14 can be a stereo phono plug, or, optionally, a locking eight (8) position connector or other suitable connector(s). Means for programming 30, shown as a personal computer, connects to the controller housing by way of interface cable 32. Advantageously, interface cable 32 is an optically coupled, electrically isolated ("opto-isolated") data cable. The interface cable 32 terminates at one end in cable plug 34, which can be miniature phone plug, for connection to the controller housing 20 and at the other end in an isolating connector 36 for connection with the means for programming 30. The isolating connector 36 can be a DB9-type connector with opto-isolating means in its base which provides sufficient electrical isolation. A vibrator 40 connects to controller housing 20 by way of vibrator lead 42 one end of which terminates in a vibrator connector 44, to provide connection to the controller housing 20. The vibrator connector 44 can be a 3.5 mm miniature stereo phono socket. Advantageously, the vibrator 40 is attached to the wheelchair of the person at a location coordinated with the area of the person's body that has sensation. The vibrator 40 can be mounted on the wheelchair frame, thus vibrating the entire chair, alerting the user. For the diabetic, this can be his or her leg or waist, for instance. The vibrator 40 thereby is an indicating means to appropriately communicate a pressure event and the requirement for some action on the part of the person. A silencing push button 50 is mounted in the controller housing 20. The silencing push button 50 is used to disable and enable, as preferred by the person, other indicating means which provide audible alarms (not shown). This allows the person to turn off any audible alarm in situations when or where it may be inappropriate or may cause embarrassment (such as in a movie theater or some social setting). The alarm can be disabled for a period of two (2) hours, or some other preferred duration as set by the means for programming 30. In these situations, the person can rely on the vibrator 40 to provide the necessary indication.

The controller housing 20 is made of plastic and measures approximately 4.8"×2.5"×0.9" and weighs approximately five ounces. Advances in electronics will, of course, allowing the size to be reduced at a reasonable cost. The controller housing 20 can be mounted anywhere using a belt clip or a holding pouch. It is preferable to mount it in close proximity to the person. For a paraplegic, for instance, mounting it on the arm, the back, or under the seat of the wheelchair. While for a diabetic mounting it on the person's shoe may be appropriate. The controller housing 20 contains the microcontroller and associated electronics including a power supply 212 (see FIG. 3). Advantageously, the vibrator 40 is a cylinder measuring about 1.0" long×0.25" diameter and vibrates at a rate between about 100 Hz and 130 Hz. Of course, different sizes and vibration rates can be used.

Figure 2:
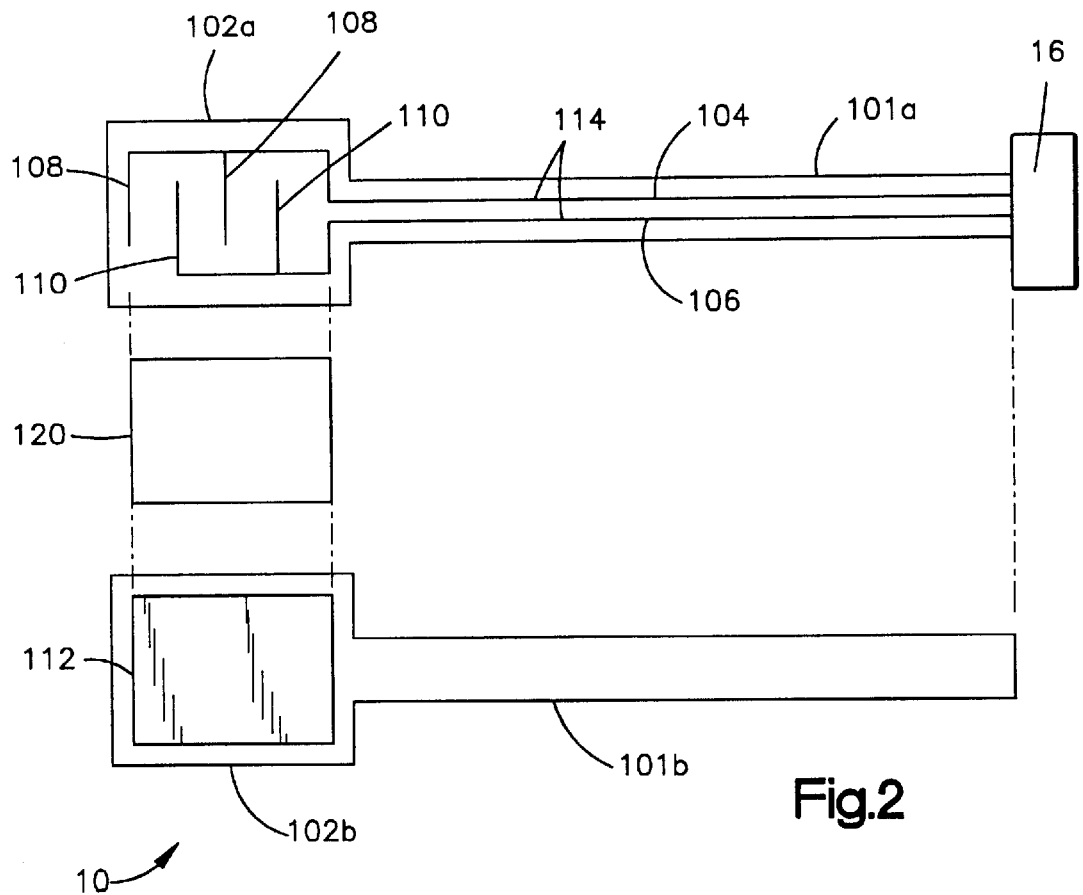
FIG. 2 is an exploded view of the sensor.

Referring now to FIG. 2 there is shown an exploded view of the sensor 10. Advantageously, the sensor 10 can be similar to the design described in U.S. Pat. No. 5,408,873 to Schmidt et al. entitled Foot Force Sensor. Sensor 10 is composed of first and second sheets 10a, 10b which are relatively thin, planar, flexible sheets of dielectric material such as polyester. Each sheet has an elongated lead section 101a, 101b, respectively, and a sensing section 102a, 102b, respectively. The inside face of the first sheet 10a has electrical contact means 114 having electrical leads 104, 106 on the first lead section 101a and a plurality of first and second poles 108, 110, respectively, on the first sensing section 102a. Advantageously, the electrical contact means 114 is a conductive silver ink printed on the inside face of the first sheet 10a but may be any type of conductive ink or element. The first and second poles 108, 110 form interlocking electrically separated fingers. The electrical leads 104, 106 terminate in lead connector 16. The inside face of second sensing section 102b is coated with a electrically resistive material 112 such as carbon ink or any equivalent material. An electrically conductive interconnect 120 is sandwiched between the first sensing section 102a and the second sensing section 102b such that it aligns with the first and second poles 108, 110 and the electrically resistive material 112. In this embodiment an Electrically Conductive Polymer Interconnect (ECPI) supplied by AT&T (Lucent Technologies) is utilized as the electrically conductive interconnect 120. The only electrical contact between the electrically resistive material 112 and electrical contact means 114 is through the electrically conductive interconnect 120. As pressure is applied to the sensing sections 102, the resistance of the sensor 10 changes, decreasing with increasing pressure. The voltage of the signal from the sensor 10 to the microcontroller 200 changes accordingly. The microcontroller 200 reads and interprets that signal as necessary to perform its functions.

Figure 3:
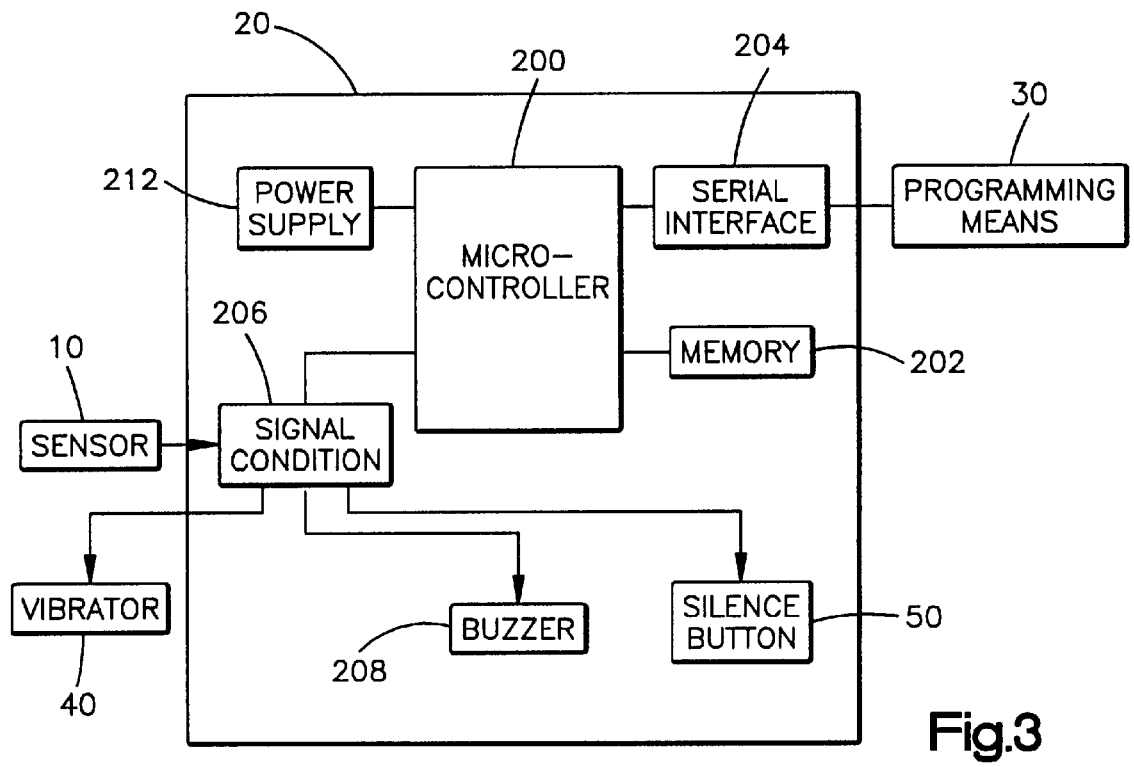
FIG. 3 is a block diagram of the present invention.

Referring now to FIG. 3 there is shown a block diagram of the present invention. The microcontroller 200, non-volatile memory 202, serial interface 204, signal conditioning means 206, buzzer 208, silencing push button 50 are located in the controller housing 20. The microcontroller 200 controls the device executing monitoring algorithms, periodic sampling of the sensor 10, generating alert and alarm signals, and recording events of interest. A non-volatile memory 202, in this embodiment an Electrically Eraseable Programmable Read-Only Memory ("EEPROM") maintains a complete record of events and stores values for the level and duration of pressure and the duration of the relief from pressure which were programmed therein by the means for programming 30. It is not necessary that any raw data be inputted into the EEPROM. The system Signal conditioning means enables the proper interface between the microcontroller and the sensor 10 and silencing push button 50, and drives the vibrator 40, and buzzer 208. The buzzer 208 is an indicating means to provide audible indications to the person when pressure relief is necessary and when such relief is past due. They are also used to provide indication of system status. A power supply 212 provides the necessary power to the device.

The microcontroller 200 has firmware which provides all the algorithms for the desired device functions, including: sensor 10 characterization, downloading operating setup from the means for programming 30, performing self-test checks, reading sensors 10, initiating relief alerts and alarms, determining if adequate reliefs are performed, detection of battery status, logging events into memory 202, and uploading logged event data to the means for programming 30. The microcontroller 200 can be the Microchip 16LC73A. This particular chip has a 32 KHz processor clock and provides 5 analog to digital converter (ADC) channels along with onboard program and scatchpad data memory and a serial interface 204 suitable for connection to the means for programming 30. The 5 ADC channels enable future expansion of the device.

Because the sensor 10 resistance decreases in a nonlinear fashion with an increase in the pressure applied thereto, the signal conditioning means 206 is designed to present an increase in voltage with increased sensor 10 conductivity, which is approximately proportional, and very nearly linear, to the applied pressure. The signal conditioning means 206 includes at least one operational amplifier ("opamp") (not shown). The opamp provides electrical isolation between the sensor 10 and other components, thus providing additional safety for the user by reducing the hazard of electrical shock. In the present invention five opamps are provided to allow for expansion. The microcontroller 200 selects one of three nonzero voltage levels at the +input of the opamp. The feedback action of the opamp then applies an equal voltage at its—input, which provides a known current through the opamp's feedback resistor. The output voltage measured with respect to the selected voltage applied to the opamp inputs then provides a direct measurement of the current flowing through both the feedback resistor and the sensor 10. The output voltage is thus proportional to the conductivity of the sensor 10 and provides a voltage within the range of the ADC in the microcontroller 200. This multiple range arrangement permits measurement of a wide range of conductivities with very low current consumption, and permits the sensor 10 to be powered down except when actually being read. This increases battery life allowing the overall package to be smaller.

Advantageously, the non-volatile memory 202 is an 8Kbyte capacity EEPROM although a larger or smaller capacity EEPROM can also be used. This provides sufficient capacity to program the various functions into the firmware; to allocate to software for storage certain desired information, such as patient ID code, name, or medical information; and to log each event, such as alerts, reliefs, arrivals in chair, departures from chair, etc. By only logging events, and not raw data, a significantly smaller EEPROM can be used than would otherwise be required. This is a significant advantage as it reduces the cost of one of the most expensive compnents of the system, thus reducing overall cost to the consumer. This capacity also enables expansion of the system and efficient uploading of data.

The power supply 212 can be standard alkaline AA cells connected in series for a total of 3 volts at 2 amp hours. Optionally, the power supply 212 can be two AAA cells to reduce size and weight of the device, or other similar battery. No other power conditioning is provided. The entire process is ratiometric obviating the need for precision regulation of the power supply 212. Low battery detection is provided so that the firmware can signal the user when battery replacement is required. This can be done either by the buzzer 208 or vibrator 40 emitting any predetermined indication such as five short sounds or vibrating periodically (such as every minute). The battery state is sensed by comparing a divided-down battery voltage against a fixed reference voltage. Accordingly, the actual threshold at which the low battery state is signaled is determined by the resistor ratio used in this divider.

Figure 4:
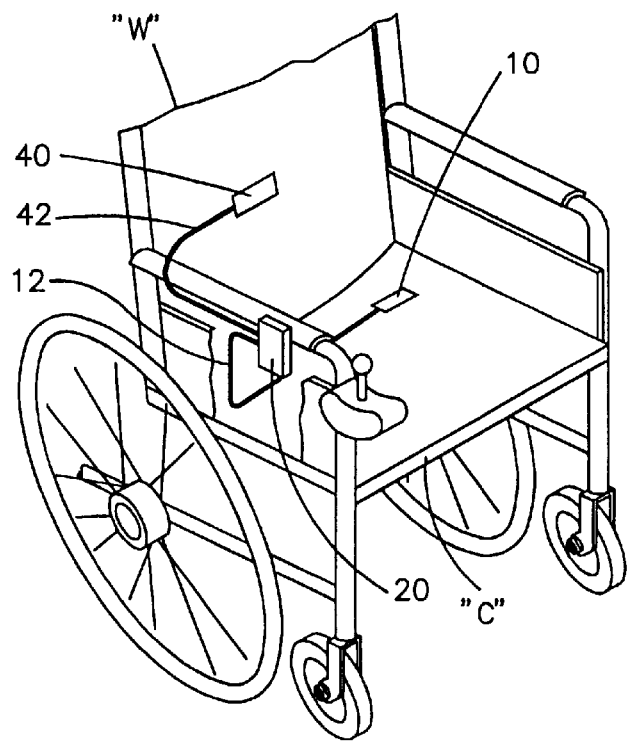
FIG. 4 is a view showing the present invention mounted on a wheelchair.

Referring now to FIG. 4, there is shown the present invention mounted on a wheelchair "W". The sensor 10 is located on or under the seat cushion "C" and provides seat pressure information to the microcontroller 200 in the controller housing 20. The controller housing 20 is shown mounted on the arm but can be mounted underneath the seat or on the seat back, or any other convenient location. After a period of time of sensed pressure (the seated pressure), the device alerts the person by some indicating means that relief is needed. The indicating means can be in the form of an audible alarm like a buzzer 208 (not shown on FIG. 4), a vibrator 40 or a combination thereof. The amount of time between the pressure reliefs and the required duration of the pressure reliefs are programmable by a physician, clinician, therapist or other health care provider using the means for programming 30 (not shown). In addition, the microcontroller 200 will log significant events (e.g., relief attempts) that may be examined later by the health care professional using the means for programming 30 after uploading the event information via the interface cable 32. Advantageously, the means for programming 30 is a personal computer which is connected to the microcontroller 200 during programming and during the uploading of recorded and logged data but is disconnected at other times allowing unrestricted movement and complete mobility of the wheelchair.

Figure 5:
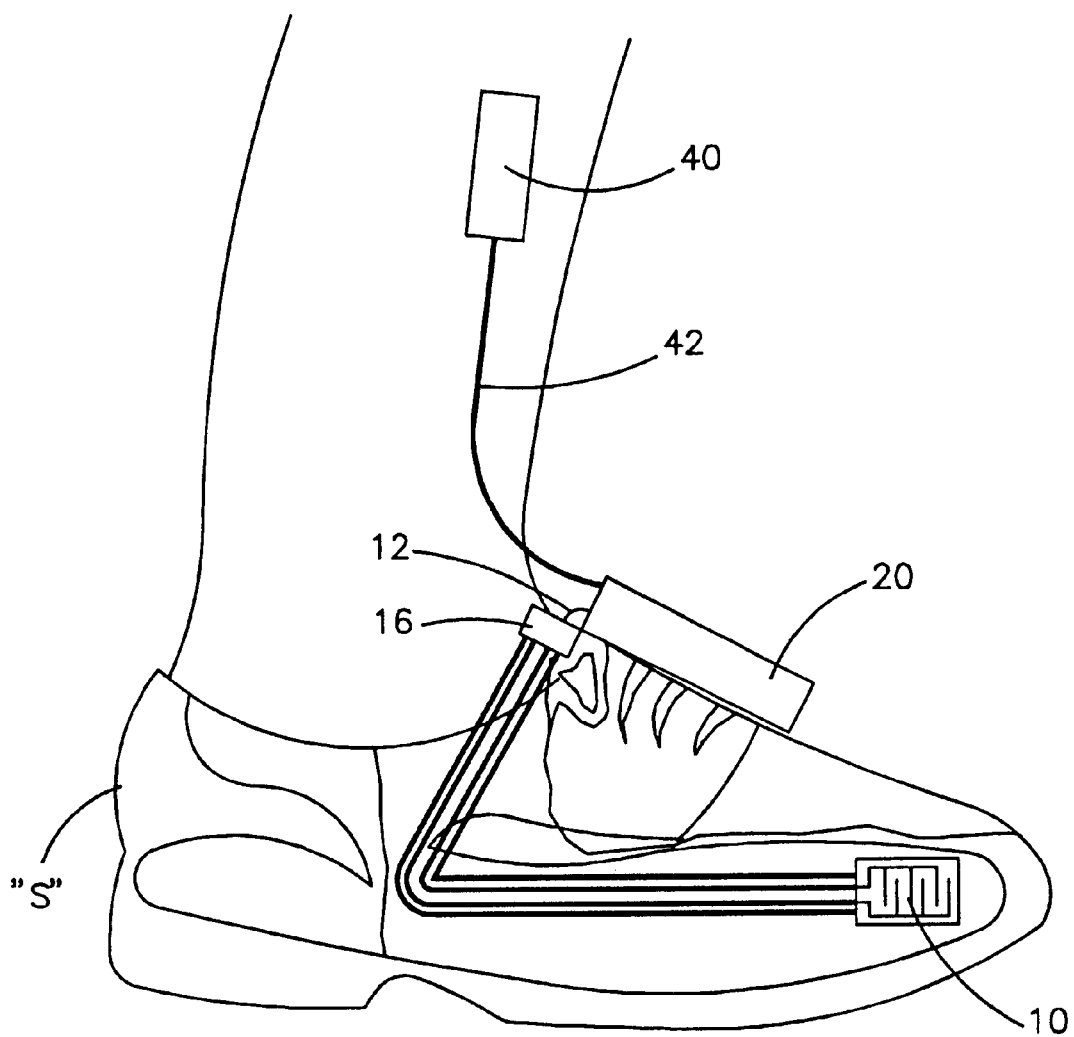
FIG. 5 is a view of the present invention mounted on a person's shoe.

Referring now to FIG. 5 there is shown a view of the present invention mounted on a person's shoe "S". In FIG. 5 the sensor 10 is placed in the shoe "S" by a metatarsal point and extends out of the shoe "S". The controller housing 20 is shown attached to the top of the shoe "S". Advantageously, the controller housing 20 may be put in a pouch to facilitate such attachment. The vibrator lead 42 extends from the controller housing 20 and connects to vibrator 40 which is shown attached to the persons leg. The vibrator 40 must be attached to the area of the person's body which has sensation. The system operates in the same manner as described above with respect to a wheelchair installation.

A pressure relief is defined as a release of pressure on the sensor 10 below some programmed threshold continuously for a minimum pressure relief duration. A pressure relief which is shorter than the minimum pressure relief duration is counted as a partial relief and can optionally produce a "continue" signal at the end of the prescribed relief time. If the accumulated relief times add up to the minimum pressure relief duration, it is counted and logged as a complete relief Any accumulated relief time is canceled upon detecting a seated pressure continuously for three minutes. If a pressure relief does not occur within a programmed interval, an alert signal will be issued via the buzzer 208 and/or the vibrator 40. If no pressure relief occurs within 30 seconds (or some other programmed interval), the first alarm is activated, and, if necessary, a second level alarm. Upon reaching this last level, the inter-relief interval is reset, and alerts or alarms will again be issued after the prescribed maximum pressure duration. The various indications can be reprogrammed based upon field testing for various combinations of tones and vibrator actions, and should normally become progressively stronger at each level. Upon detecting a valid relief, the system notifies the user of this fact. All reliefs are logged to the memory 202 along with the circumstances surrounding them, for example, whether prompted by the system or initiated by the user without prompting, how long from the initial alert, etc.

The system can provide audible alerts with a choice of tone, pitch, volume or intermittency. For instance some tonal frequencies may include, but are not limited to, 1365 Hz, 1638 Hz, 2048 Hz, 2731 Hz, and 4096 Hz, and may consist of a warble, a chirp, or an upward sweep (increasing frequency) of tones. The audible alert sounds for approximately the first 100 mSec of each second, and can be repeated for between 1 and 15 seconds. Alternately, or additionally, the vibrator 40 can be actuated for a similar duty cycle. An example of a particular alert configuration can be as follows: an intermittent 2048 Hz tone, pulsing for 100 mSec of each second of programmable duration (1 to 15 seconds, default 6 seconds) for the alert; the first level alarm uses the same pattern at 2731 Hz; the final alarm uses the warble between 2731 Hz and 4096 Hz; and a chirp indicates the completion of the prescribed relief time. Reducing the duty cycle of the alerts to the first 100 mSec of each second allows significant power saving in the system, thus lowering weight, power and volume requirements.

The firmware is programmable as may be desired for the specific application. In this particular embodiment it is based on a do-forever loop which executes once each second. The idle time in each one second cycle includes monitoring of the serial port and execution of any externally entered commands. When the clock ticks, the master time (time used for logging events) is updated, and the pressure is compared to the non-seated pressure and debounced. Two linked timers, "TimeOn" and "TimeOff" are updated for use in succeeding logic according to the one or more sensors 10. A timer "SinceRelief" is incremented to show the elapsed time since a valid relief was recognized. On the transition to "OnSeat", if TimeOff exceeds 3 minutes, an arrival indication is generated, serving as a system start-up self test; in order to generate this indication, all major sections of the system must be operational. A complete relief (or an accumulation of partial reliefs after the user is prompted) resets the inter-relief timer and alert/alarm logic.

The system provides a quantitative means to allow the determination of a specific maximum pressure duration and a minimum pressure relief duration for a person on an individual basis. As an example for wheelchair applications, this is done by logging and analyzing seated pressure and non-seated pressure in order to differentiate between them such that the system is characterized for each user, cushion and seat combination. To do this, the system is installed with the sensor 10 located on a wheelchair. The microcontroller 200 is connected to the means for programming 30 by way of the interface cable 32, through serial interface 204. The user is asked to sit normally, then perform a relief, and to repeat this procedure several times, typically five. The means for programming 30 contains software which will then average the seated and non-seated pressure readings taken and determine average sensor 10 value for both seated and non-seated pressures. The overall average between the seated and the non-seated pressures is then used to determine if the current pressure is above or below the overall average to determine if the person is seated or non-seated. Other similar techniques may also be used to determine seating status and standing status. The user can then perform several trial reliefs to verify proper operation of the system. Using the means for programming 30 the physician, clinician and/or therapist then programs the operating parameters for the system. The physician, clinician and/or therapist will have the option of configuring the system in basic setup or advanced setup. Basic setup requires minimal information input from the physician, clinician and/or therapist, either using set default values or selecting from a limited choice of range settings. Advanced setup allows complete control of all operating parameters, also providing additional range and operational settings not available in the basic setup. The same process can be applied to situations involving diabetics, with standing pressure and sitting pressure exerted on a foot.

Figure 6:
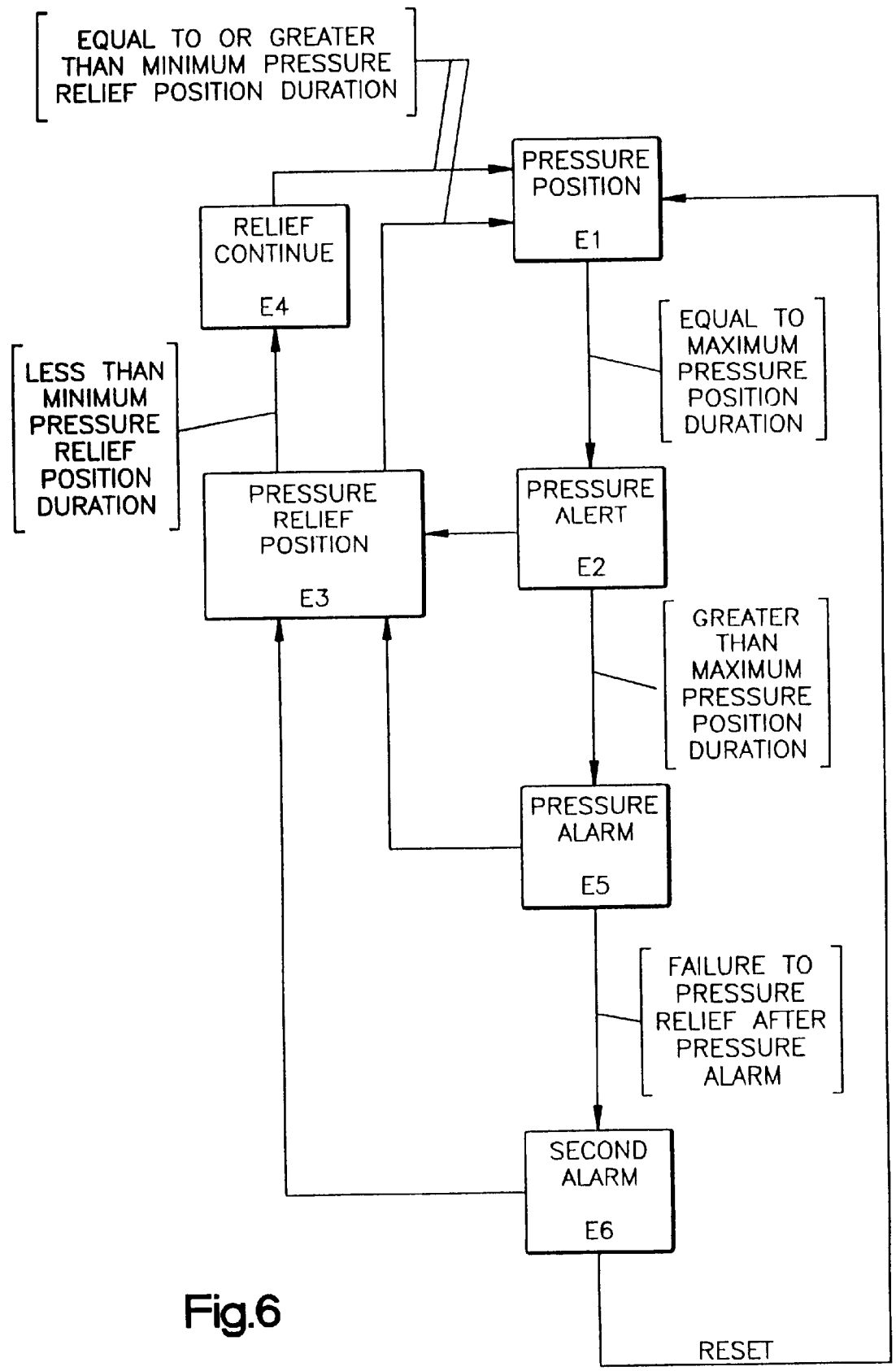
FIG. 6 is a flowchart showing the operation of an embodiment of the invention.

Referring now to FIG. 6, there is shown a flowchart of the operation of the reminder mode of the invention. The reminder mode of the system can be used by a physician, clinician and/or therapist as a method to train the user in the proper manner to perform pressure reliefs. With the user in a pressure position (seated for a paraplegic standing for a diabetic) El the sensor 10 measures the pressure and the system begins to measure the duration the user is in the pressure position. An initial time delay is incorporated into the system to assure that system is responding to a user in a pressure position and not some other load, or even handling of the wheelchair. When the pressure duration equals the programmed maximum pressure duration a relief alert E2 is given. This will activate an indicating means; either the sounding of the buzzer 208 with a pulsing tone or an activation of the vibrator 40. If the user initiates a pressure relief (paraplegic lifting himself from the wheelchair or a diabetic sitting down) the system will time the duration of the pressure relief E3. When the user completes the pressure relief (sensor 10 detects pressure) the system will determine if the pressure relief duration equals or exceeds the minimum pressure relief duration. If it does, the system again counts the time the user is in the pressure position.

If the pressure relief is less than the minimum pressure relief duration, the system will prompt the user to perform a relief continue E4 by activating an indicating means by sounding the buzzer 208 or activating the vibrator 40. The buzzer 208 will repeatedly sound or the vibrator 40 will activate until the sum of the duration of all pressure reliefs attempted equal or exceed the programmed minimum relief duration. If the relief continue prompt is ignored, after 5 seconds the system will reset the timer count for the maximum pressure duration, starting the monitoring cycle over. If there is no response to the relief alert, a relief alarm E5 warning will be given after the relief alert. This may be a quicker audible pulsing tone or activation of the vibrator 40. If there is still no response, a second alarm E6 will be given. This second alarm may be a pulsing, warbled tone alternating between two or more different frequencies from the buzzer 208 or an activation of the vibrator 40.

If all alerts and alarms are ignored the system will reset the timer counter for the maximum pressure duration starting the training cycle over. If a sufficient relief occurs before the relief alert is given, then the system will detect this and reset the timer count for the maximum pressure duration, starting the training cycle over.

A particular embodiment of the invention has been described, but those skilled in the art will recognize that many modifications are possible that will achieve the same goals by substantially the same system, device or method, and where those systems, devices or methods still fall within the true spirit and scope of the invention disclosed. Therefore the invention should be considered to be limited in scope only in accordance with the following claims.

What is claimed is:

1. A pressure relief reminder and compliance system to prevent the formation of pressure sores on a person's skin, comprising:

a. a sensor which responds according to the pressure exerted on the skin;

b. a programmable microcontroller connected to said sensor, said microcontroller changeably programmable with certain values of pressure and time, such that the level and duration of such pressure and the duration of the absence of such pressure are compared to said values and recorded, c. means for programming said values into said microcontroller; and d. indicating means connected to said programmable microcontroller such that indication is provided that said values have been reached.

2. The pressure relief reminder and compliance system of claim 1 further comprising interfacing means between said microcontroller and said means for programming.

3. The pressure relief reminder and compliance system of claim 1 wherein said means for programming is a personal computer.

4. The pressure relief reminder and compliance system of claim 1 wherein said values recorded by said microcontroller can be uploaded into said means for programming and displayed thereon.

5. The pressure relief reminder and compliance system of claim 1 wherein said indicating means is a vibrator.

6. The pressure relief reminder and compliance system of claim 1 wherein said indicating means is an audible alarm.

7. The pressure relief reminder and compliance system of claim 1 wherein said sensor comprises flexible sheets of dielectric material.

8. The pressure relief reminder and compliance system of claim 6 further comprising a silencing push button whereby said audible alarm can be deactivated.

9. A method for training a person to reduce the incidence of pressure sores occurring due to pressure being exerted on the skin for a certain duration, comprising the steps of:
   a. providing a quantitative means to allow the determination of a specific maximum pressure duration and a minimum pressure relief duration for the person;
   b. measuring the duration of the person in a pressure position;
   c. alerting the person when the duration of said pressure position equals said maximum pressure duration;
   d. alarming the person when the duration of said pressure position exceeds said maximum pressure duration;
   e. continuing said alarming until the person is in a pressure relief position,
   f. measuring the duration of said pressure relief position; and
   g. prompting the person to continue said pressure relief position until the duration thereof equals said minimum pressure relief duration.

10. The method of claim 9 wherein said alerting is performed by an audible indicating means.

11. The method of claim 9 wherein said alerting is performed by a vibratory indicating means.

12. The method of claim 9 wherein said alarming is performed by an auditory indicating means.

13. The method of claim 9 wherein said alarming is performed by a vibratory indicating means.

14. The method of claim 9 wherein said prompting is performed by an auditory indicating means.

15. The method of claim 9 wherein said prompting is performed by a vibratory indicating means.

16. The method of claim 9 wherein said quantitative means comprises the steps of logging and analyzing pressure position pressure and pressure relief position pressure.

* * * * *